United States Patent
Tomomura

(10) Patent No.: US 10,111,627 B2
(45) Date of Patent: Oct. 30, 2018

(54) MEDICAL IMAGE PROCESSING APPARATUS

(71) Applicant: TOSHIBA MEDICAL SYSTEMS CORPORATION, Otawara-Shi (JP)

(72) Inventor: Kenji Tomomura, Nasushiobara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 212 days.

(21) Appl. No.: 15/277,016

(22) Filed: Sep. 27, 2016

(65) Prior Publication Data

US 2017/0086774 A1   Mar. 30, 2017

(30) Foreign Application Priority Data

Sep. 30, 2015  (JP) ................. 2015-193593
Aug. 31, 2016  (JP) ................. 2016-169226

(51) Int. Cl.
*A61B 6/00* (2006.01)
*A61B 6/03* (2006.01)
*A61B 6/06* (2006.01)

(52) U.S. Cl.
CPC ........... *A61B 6/032* (2013.01); *A61B 6/06* (2013.01); *A61B 6/4035* (2013.01); *A61B 6/4488* (2013.01); *A61B 6/566* (2013.01)

(58) Field of Classification Search
CPC ......... A61B 6/032; A61B 6/4488; A61B 6/06; A61B 6/4035; A61B 6/566; G01T 1/2928; H04N 5/361; H04N 5/3698
USPC ...................................................... 378/4–20
See application file for complete search history.

(56) References Cited

U.S. PATENT DOCUMENTS

2002/0044211 A1   4/2002   Tujii et al.
2015/0234058 A1*  8/2015   Engel ................. G01T 1/241
                                            250/370.08

FOREIGN PATENT DOCUMENTS

JP   7-313501      12/1995
JP   9-276263      10/1997
JP   2002-165142   6/2002
JP   2012-147949   8/2012

* cited by examiner

*Primary Examiner* — Courtney Thomas
(74) *Attorney, Agent, or Firm* — Oblon, McClelland, Maier & Neustadt, L.L.P.

(57) ABSTRACT

According to one embodiment, a radiation diagnostic apparatus includes an X-ray tube, radiation detecting elements, signal processing substrates, and processing circuitry. The signal processing substrates performs processing including at least A/D conversion processing on outputted signals of the radiation detecting elements and outputs processed signals as the outputted signals subjected to the processing. The processing circuitry identifies a non-observing element or a non-observing substrate based on information on an imaging region included in imaging conditions of an object, the non-observing element being a radiation detecting element of the radiation detecting elements which corresponds to a region other than the imaging region, and the non-observing substrate being a signal processing substrate of the signal processing substrates which corresponds to the non-observing element. The processing circuitry further controls an operation of the non-observing element or an operation of the non-observing substrate in imaging under the imaging conditions.

17 Claims, 10 Drawing Sheets

MEDICAL IMAGE PROCESSING APPARATUS

CROSS-REFERENCE TO RELATED APPLICATIONS

This application claims the benefit of priority of Japanese Patent Application No. 2015-193593, filed Sep. 30, 2015, and Japanese Patent Application No. 2016-169226, filed Aug. 31, 2016, the entire contents of all of which are incorporated herein by reference.

FIELD

Embodiments described herein relate generally to a radiation diagnostic apparatus.

BACKGROUND

A radiation diagnostic apparatus such as an X-ray CT (Computed Tomography) apparatus, an X-ray angiographic apparatus, and an X-ray diagnostic apparatus includes a radiation detector configured to detect X-rays which have been radiated from an X-ray source and have passed through an object. In general, plural radiation detecting elements are arranged in a radiation detector. A radiation detector with multiple radiation detecting elements arranged therein is quite useful because it can detect a wide range of X-rays.

A radiation diagnostic apparatus equipped with a radiation detector in which plural radiation detecting elements are arranged acquires all output data outputted by all of the radiation detecting elements of the radiation detector in X-ray imaging of an object. However, output data of detecting element whose position is corresponding to a region other than an imaging region of the object (hereinafter, the region other than the imaging region is referred to as a non-observing region) are unnecessary data excluding a case where the output data corresponding to the non-observing region are required (e.g., a case where such data are used in post-processing).

Thus, it has to be said that it is a waste of electric power to acquire output data of detecting elements corresponding to the non-observing region, unless the output data of such detecting elements are required.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of a radiation diagnostic apparatus according to embodiments of the present invention with reference to the drawings.

In general, according to one embodiment, a radiation diagnostic apparatus includes an X-ray tube, plural radiation detecting elements, plural signal processing substrates, and processing circuitry. The plurality of radiation detecting elements detects X-rays radiated from the X-ray tube. The plurality of signal processing substrates performs processing including at least A/D conversion processing on outputted signals of the plurality of radiation detecting elements and outputs processed signals as the outputted signals after being subjected to the processing including at least A/D conversion. The processing circuitry identifies a non-observing element or a non-observing substrate based on information on an imaging region included in imaging conditions of an object, the non-observing element being a radiation detecting element of the plurality of radiation detecting elements which corresponds to a region other than the imaging region, and the non-observing substrate being a signal processing substrate of the plurality of signal processing substrates which corresponds to the non-observing element. The processing circuitry further controls an operation of the non-observing element or an operation of the non-observing substrate in imaging under the imaging conditions.

According to one embodiment, a radiation diagnostic apparatus reduces its power consumption by limiting acquisition of output data of radiation detecting element corresponding to the non-observing region which is a region except an imaging region. Hereinafter, a radiation detecting element whose position being corresponding to the non-observing region is referred to as "a non-observing element". The limitation of acquiring output data of each non-observing element may be performed by limiting an operation of a signal processing circuit which is disposed to a post-stage of each non-observing element.

In the following description, an X-ray CT apparatus will be used as an example of the radiation diagnostic apparatus.

Figure 1:
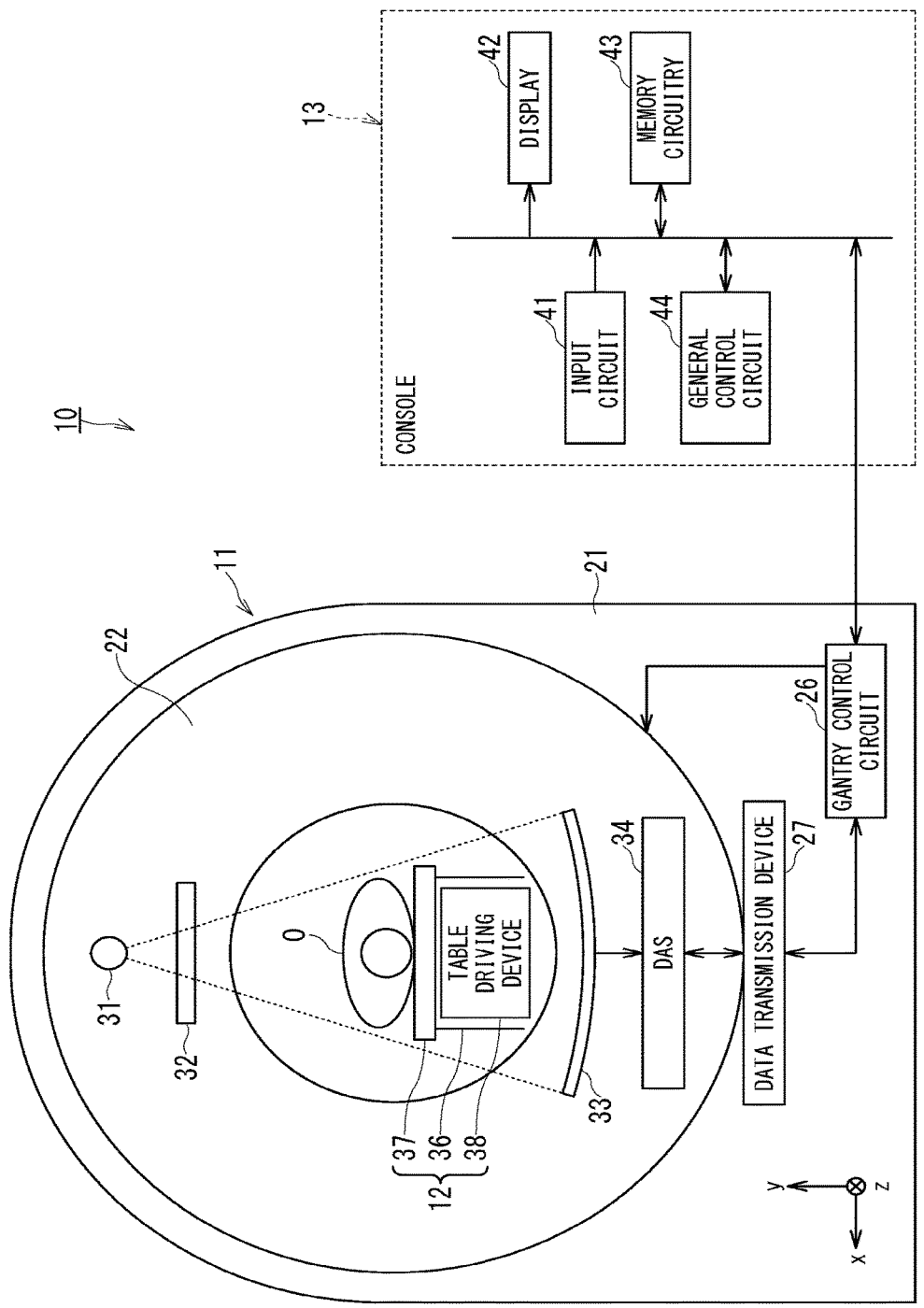
FIG. 1 is a block diagram illustrating overall configuration of an X-ray CT apparatus in one embodiment.

FIG. 1 is a block diagram illustrating overall configuration of an X-ray CT apparatus 10 in one embodiment. Although FIG. 1 shows a case where the X-ray CT apparatus 10 configured as a so-called third generation CT apparatus, i.e., an R/R (Rotate/Rotate) type in which an X-ray tube and an X-ray detector integrally rotate about an object, the X-ray CT apparatus 10 is not limited to such a type. For instance, the X-ray CT apparatus 10 may be configured as a so-called fourth generation CT apparatus, i.e., an S/R (Stationary/Rotate) type or an N/R (Nutate/Rotate) type in which multiple detecting elements are circularly arrayed and only the X-ray tube rotates about an object.

Additionally, in recent years, productization of an X-ray CT apparatus of so-called multi-tube type in which plural pairs of X-ray tubes and X-ray detectors are mounted on a rotating ring has been advanced, and its peripheral technology has been developed. The X-ray CT apparatus 10 of the present embodiment is applicable to both of a single-tube type and a multi-tube type. In the following, a case where the X-ray CT apparatus 10 is configured as a single-tube type will be described as one aspect of the present embodiment.

As shown in FIG. 1, the X-ray CT apparatus 10 includes a gantry 11, a bed 12, and a console 13.

The gantry 11 includes a fixed base 21 and a rotating body 22. The fixed base 21 is fixed to an installation surface such as a floor surface, and includes a gantry control circuit 26 and a data transmission device 27. The rotating body 22 integrally supports an X-ray tube 31, a diaphragm 32, an X-ray detector 33, and a DAS (Data Acquisition System) 34, and rotates about its opening formed at its central part.

In the present embodiment, the direction in parallel with the rotational axis of the rotating body 22 is defined as a z-axis direction, and the direction of the normal line of the installation surface of the fixed base 21 is defined as a y-axis direction. Further, the direction which is in parallel with the installation surface and orthogonal to the z-axis direction is defined as an x-axis direction (see the bottom left corner in FIG. 1).

The X-ray tube 31 is supplied with high voltage generated by a non-illustrated high-voltage power source of the fixed base 21 via, e.g., a slip-ring under the control of the gantry control circuit 26. Incidentally, the high-voltage power source may be disposed in the rotating body 22.

X-rays generated by the X-ray tube 31 are radiated as fan beam X-rays or cone beam X-rays toward the object O.

The diaphragm 32 is configured of, e.g., a wedge filter. The diaphragm 32 adjusts the irradiation range of X-rays radiated from the X-ray tube 31 in at least one of the channel direction and the slice direction (i.e., the column direction which is also defined as the z-axis direction), under the control of the gantry control circuit 26.

The X-ray detector 33 is configured of plural X-ray detecting elements (i.e., charge storage elements). These X-ray detecting elements (radiation detecting elements) detect X-rays which have been radiated from the X-ray tube 31 and have passed through the object O. The X-ray tube 31 and the X-ray detector 33 are supported by the rotating body 22 at such a position that the X-ray tube 31 and the X-ray detector 33 face each other with the object O loaded on the bed 12 interposed therebetween.

As the above-described X-ray detector 33, for instance, a so-called one-dimensional array type (i.e., a single-slice type) may be used. In the one-dimensional array type of X-ray detector, X-ray detecting elements are arrayed in one column in the slice direction (i.e., the z-axis direction) and in plural rows in the channel direction perpendicular to the slice direction.

Additionally, a so-called two-dimensional array type (i.e., a multi-slice type) equipped with X-ray detecting elements arrayed in plural columns in the slice direction and in plural rows in the channel direction may be used as the X-ray detector 33. In the case of the multi-slice type, an X-ray detector in which plural columns of X-ray detecting elements are arrayed in the slice direction (i.e., the z-axis direction) and each of those plural columns includes plural channels in the channel direction may be used.

Moreover, in the case of the two-dimensional array type, the X-ray detector 33 may be configured of plural X-ray detecting elements densely-arrayed as to both of the slice direction (i.e., the z-axis direction) and the channel direction. Hereinafter, a description will be given of a case where the X-ray detector 33 is configured of plural X-ray detecting elements two-dimensionally and densely arrayed on a plane defined by the slice direction axis (i.e., the first axis) and the channel direction axis (i.e., the second axis).

The DAS 34 receives analogue signals outputted from the plural X-ray detecting elements of the X-ray detector 33, and performs signal processing such as current/voltage conversion, amplification, and A/D (analogue to digital) conversion on the received analogue signals. Afterward, the DAS 34 generates transmission data by using the digitized signals subjected to the above-described signal processing, and transmits the transmission data to the console 13 via the data transmission device 27. The console 13 performs reconstruction processing based on projection data included in the transmission data so as to generate reconstructed images.

The rotating body 22 integrally supports the X-ray tube 31, the diaphragm 32, the X-ray detector 33, and the DAS 34 and is supported by the fixed base 21. The rotating body 22 rotates under the control of the gantry control circuit 26, which causes the entirety of the X-ray tube 31, the diaphragm 32, the X-ray detector 33, and the DAS 34 to integrally rotate about the object O, i.e., about the opening formed in the central part of the rotating body 22. Additionally, the rotating body 22 may be configured so that the rotating body 22 can tilt with respect to the fixed base 21. Information on the current rotational speed of the rotating body 22 and information on a tilt operation and the current tilt angle are inputted to the console 13 via the gantry control circuit 26.

The bed 12 includes a base 36 installed on the installation surface such as the surface floor, a table 37 supported by the base 36, and a table driving device 38.

The table 37 is configured so that the object O can be loaded thereon.

The table driving device 38 upwardly and downwardly moves the table 37 in the y-axis direction (i.e., the vertical direction) under the control of the gantry control circuit 26. Additionally, the table driving device 38 moves the table 37 to the X-ray irradiation field at the opening formed in the central part of the rotating body 22 along the z-axis direction (i.e., the longitudinal direction of the table 37), under the control of the gantry control circuit 26. Further, the table driving device 38 moves the table 37 in the x-axis direction (i.e., the width direction of the table 37) under the control of the gantry control circuit 26. Moreover, the table driving device 38 can slew the table 37 around each of the x-axis, the y-axis, and the z-axis under the control of the gantry control circuit 26.

Information on movement of the table 37 (i.e., moving speed and a moving direction) and information on the current position of the table 37 are inputted to the console 13 via the table driving device 38 and the gantry control circuit 26.

The gantry control circuit 26 includes at least a processor and a memory circuit. The gantry control circuit 26 performs X-ray imaging of the object O by controlling the gantry 11 according to programs stored in the memory circuit, under the control of the console 13.

Although a description has been given of a case where the gantry control circuit 26 and the console 13 are connected with each other by wire in FIG. 1, the gantry control circuit 26 and the console 13 may be interconnected via a network so that transmission and reception of data can be performed therebetween.

The data transmission device 27 performs parallel/serial conversion, electro-optical/opto-electrical conversion, and serial/parallel conversion on the transmission data outputted from the DAS 34. The data transmission device 27 includes, e.g., a parallel/serial converter, an electro-optical/opto-electrical converter, and a serial/parallel converter (not illustrated). Transmission data of plural channels outputted from the DAS 34 are converted into time-sequential data of one channel by the parallel/serial converter disposed in the rotating body 22, and then inputted to the serial/parallel converter disposed in the fixed base 21 by means of communication such as optical communication using the electro-optical/opto-electrical converter.

Afterward, the time-sequential data of one channel are converted into transmission data of plural channels by the above-described serial/parallel converter. The time-sequentially obtained projection data of plural channels are stored in the console 13 together with accompanying information. Specifically, arrangement position information of the radiation detecting elements in the channel direction, rotational angle information, positional information of the projection data in the slice direction (i.e., an imaging position) are added to the projection data of plural channels as the accompanying information.

As long as data transmission between the DAS 34 disposed in the rotating body 22 and the gantry control circuit 26 disposed in the fixed base 21 is practicable, a data transmission method performed by the data transmission device 27 is not limited to the above description. For instance, a device such as a slip-ring may be used for the data transmission performed by the data transmission device 27, and data transmission may be performed in a contactless manner.

The console 13 of the X-ray CT apparatus 10 is configured of, e.g., a general personal computer and/or a workstation. The console 13 includes an input circuit 41, a display 42, a memory circuitry 43, and a general control circuit 44. Incidentally, it is not necessary that the console 13 is independently provided. One or some of the components 41 to 44 of the console 13 may be separately disposed in the gantry 11.

The input circuit 41 is configured of a general input device such as a trackball, a switch button, a mouse, a keyboard, and a numerical keyboard. The input circuit 41 outputs an operational input signal corresponding to a user's operation to the general control circuit 44. For instance, a user can set a scan plan (imaging conditions) via the input circuit 41. In the present embodiment, imaging conditions are assumed to include information on the imaging region (i.e., an FOV: Field Of View) defined in the channel direction and in the slice direction. Imaging conditions may be set via the input circuit 41 or may be acquired via a network.

The display 42 is configured of a general display output device such as a liquid crystal display, an OLED (Organic Light Emitting Diode) display, and displays images such as a reconstructed image under the control of the general control circuit 44.

The memory circuitry 43 is equipped with configuration including memory media which can be read by a processor such as a magnetic memory medium, an optical memory medium, and a semiconductor memory. The memory circuitry 43 may be configured so that some or all of the programs and data stored in those memory media can be downloaded by means of communication via an electronic network. The memory circuitry 43 stores, e.g., projection data transmitted from the DAS 34 and reconstructed images generated by the general control circuit 44.

The general control circuit 44 is a processor configured to perform processing of controlling the gantry 11 via the gantry control circuit 26 and processing of generating reconstructed images based on the projection data, by reading out and executing programs stored in the memory circuitry 43. For instance, when imaging condition are set by a user via the input circuit 41, the general control circuit 44 executes X-ray imaging of the object O by controlling the gantry 11 via the gantry control circuit 26 on the basis of those imaging conditions.

Figure 2:
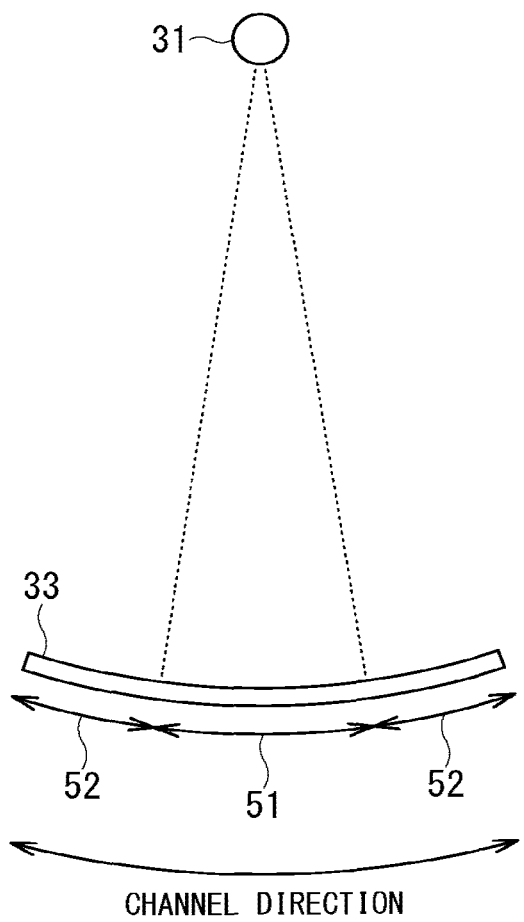
FIG. 2 is a schematic diagram illustrating relationship between an X-ray detector and an imaging region.

FIG. 2 is a schematic diagram illustrating relationship between the X-ray detector 33 and the imaging region 51.

Depending on imaging conditions, the imaging region 51 is sometimes narrower than the arrangement region of all the X-ray detecting elements of the X-ray detector 33. In this case, output data of the respective X-ray detecting elements corresponding to non-observing regions 52 as a region other than the imaging region 51, i.e., output data of the non-observing elements, are unnecessary data, except some cases where data of those non-observing elements are needed in, e.g., post-processing.

When a non-observing region 52 exists in the arrangement region of all the X-ray detecting elements and output data of non-observing elements are unnecessary according to imaging conditions, power consumption of the X-ray CT apparatus 10 can be reduced in imaging under such imaging conditions by reducing power consumption required for acquiring output data of each non-observing element in the following manner. That is, only the components (X-ray detecting elements 33a and A/D conversion substrates) related to acquisition of output data of the X-ray detecting elements 33a corresponding to the imaging region included in the imaging conditions are caused to operate, while an operation of each non-observing element or an operation of each non-observing substrate is limited.

Figure 3:
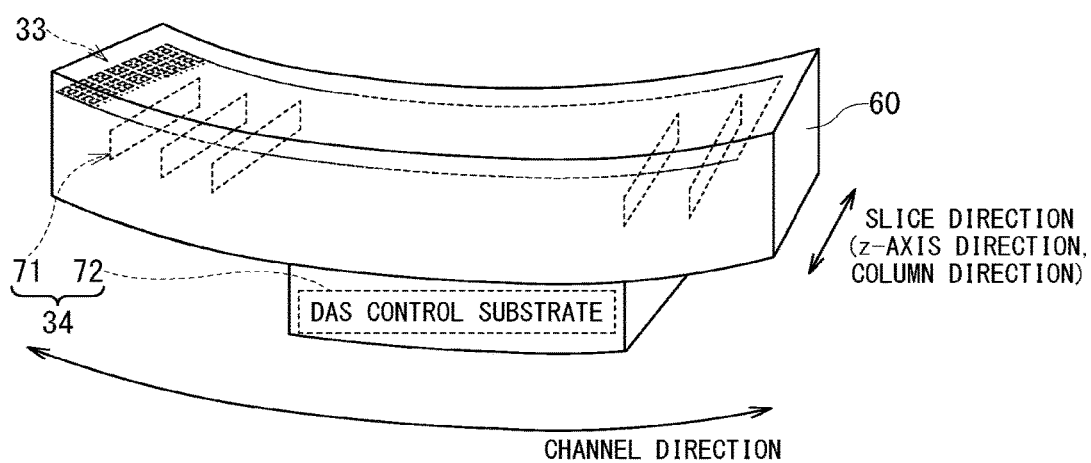
FIG. 3 is a schematic perspective view illustrating a housing in which the X-ray detector and a DAS (Data Acquisition System) are housed.

FIG. 3 is a schematic perspective view illustrating a housing 60 in which the X-ray detector 33 and the DAS 34 are housed. Additionally, FIG. 4 is a block diagram illustrating internal configuration of the DAS 34.

As shown in FIG. 3, the X-ray detector 33 and the DAS 34 are, for instance, housed in one common housing 60. The DAS 34 includes a DAS control substrate 72 and a conversion-substrate set 71 which is configured of signal processing substrates (hereinafter, referred to as A/D conversion substrates in the present embodiment) ADC1, ADC2, . . . , and ADCn, where n is a positive integer. Each of the A/D conversion substrates ADC1 to ADCn is equipped with signal processing circuits such as an A/D converter and a current/voltage converter configured to receive data from each X-ray detecting element 33a. Incidentally, the housing 60 may be provided with a protruding part for supporting the DAS control substrate 72 (see FIG. 3).

Figure 4:
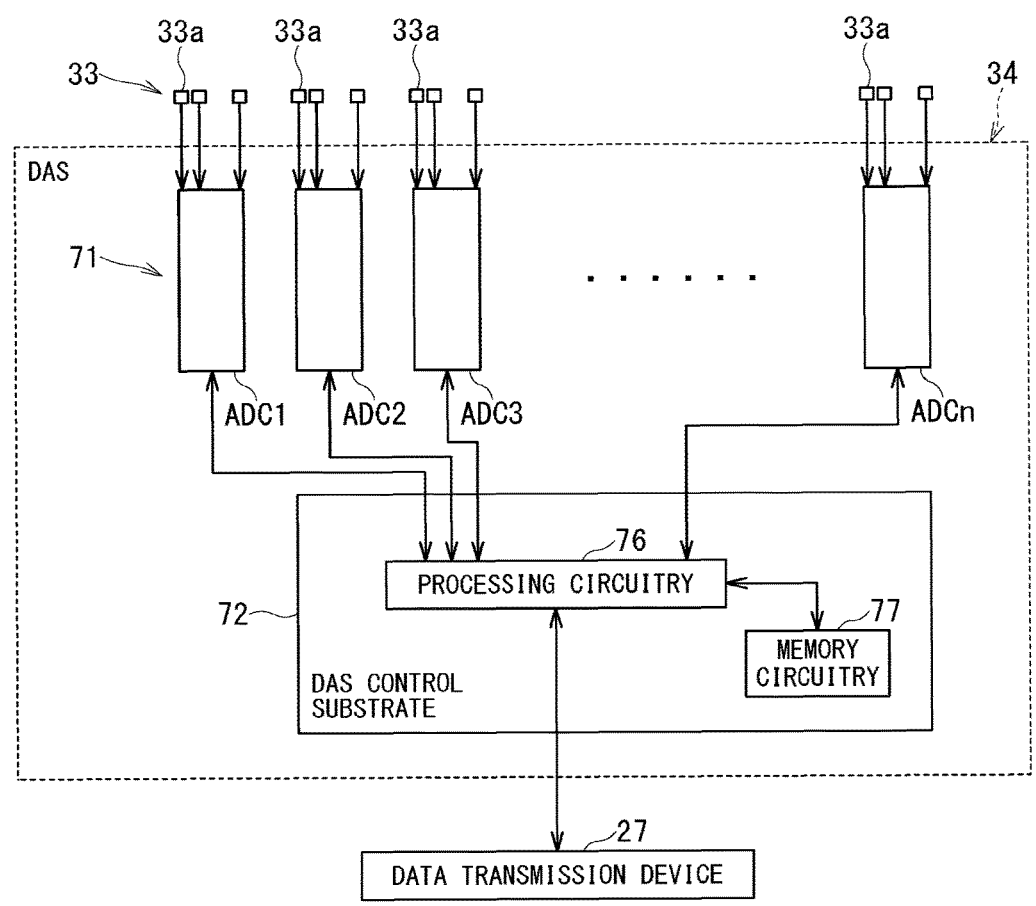
FIG. 4 is a block diagram illustrating internal configuration of the DAS.

As shown in FIG. 4, the DAS control substrate 72 includes processing circuitry 76 and memory circuitry 77.

The processing circuitry 76 is a processor configured at least to perform processing for causing only the components corresponding to the imaging region 51 included in the imaging conditions to operate in imaging under the imaging conditions, by reading out and executing programs stored in the memory circuitry 77. The components corresponding to the imaging region 51 are the components (i.e., X-ray detecting elements 33a and A/D conversion substrates)

necessary for acquiring outputted data of the X-ray detecting elements 33a being corresponding to the imaging region 51.

The memory circuitry 77 is equipped with configuration including memory media which can be read by a processor such as a magnetic memory medium, an optical memory medium, and a semiconductor memory. The memory circuitry 77 may be configured so that some or all of the programs and data stored in those memory media can be downloaded by means of communication via an electronic network. Detailed configuration of the processing circuitry 76 will be described below with reference to FIG. 8.

As shown in FIG. 4, the processing circuitry 76 communicates with the conversion-substrate set 71. Each of the A/D conversion substrates (i.e., the signal processing substrates) ADC1 to ADCn of the conversion-substrate set 71 receives output from plural X-ray detecting elements 33a.

Each of the A/D conversion substrates ADC1 to ADCn of the conversion-substrate set 71 receives respective outputted signals of plural X-ray detecting elements 33a constituting the X-ray detector 33, and performs processing including at least A/D conversion on the outputted signals and outputs processed signals, i.e., the processed outputted signals subjected to the processing including at least A/D conversion. Each of the A/D conversion substrates ADC1 to ADCn may perform further processing such as current/voltage conversion and amplification on the respective outputted signals of plural X-ray detecting elements 33a.

Incidentally, another substrate in which processing except A/D conversion such as current/voltage conversion and amplification is performed on the respective outputted signals of plural X-ray detecting elements 33a may be further provided. In this case, the A/D conversion substrates (signal processing substrates) described in the present embodiment mean a collective term including the substrates for performing A/D conversion and the above-described substrate for performing processing except A/D conversion.

The processing circuitry 76 controls state transition of each of the A/D conversion substrate ADC1 to ADCn of the conversion-substrate set 71 so that each of the A/D conversion substrate ADC1 to ADCn operates in one of three operational states including a normal operation state, a standby state, and a stop state. The normal operation state is a state where operations such as A/D conversion on the respective outputted signals of X-ray detecting elements 33a and output of the processed signals are performed. The standby state is a state where at least the operation of outputting the processed signals is stopped. The stop state is a state where power-supply to the A/D conversion substrates ADC1 to ADCn is stopped and all the operations are stopped. Each of the standby state and the stop state is a state where the operation of outputting the processed signals is stopped. In the following description, the standby state and the stop state may be referred to as an operation-limited state.

In imaging under the imaging conditions, the processing circuitry 76 of the present embodiment limits acquisition of output data of non-observing elements and causes only the components corresponding to the imaging region 51 included in the imaging conditions to operate (i.e., the X-ray detecting elements 33a and the A/D conversion substrate both of which correspond to the imaging region 51 determined by the imaging conditions are caused to operate by the processing circuitry 76). Thus, the processing circuitry 76 can reduce power consumption compared with the case of causing all the X-ray detecting elements 33a to operate in imaging.

Specifically, in imaging under the imaging conditions, the processing circuitry 76 controls the X-ray detecting elements 33a and the A/D conversion substrate both of which correspond to the imaging region 51 so that such X-ray detecting elements 33a and A/D conversion substrate are in the normal operation state where processed signals can be outputted. At the same time, in imaging under the imaging conditions, the processing circuitry 76 controls each non-observing element and/or each non-observing substrate so that acquisition of output data of each non-observing element is limited. In other words, the processing circuitry 76 controls them so that each non-observing substrate is in an operation-limited state or each non-observing element is in a stop state.

There are two main methods in methods of driving A/D conversion substrates as follows. One of them is a driving method in which all the A/D conversion substrates are in the normal operation state unless otherwise specifically controlled (hereinafter, referred to as an originally-ON method). The other of them is a driving method in which all the A/D conversion substrates are in the operation-limited state (e.g., in the stop state) unless otherwise specifically controlled (hereinafter, referred to as an originally-OFF method).

When the driving method of the A/D conversion substrates is the originally-ON method, the processing circuitry 76 performs processing of reducing power consumption of the X-ray CT apparatus 10 by limiting the acquisition operation of output data of the X-ray detecting elements 33a corresponding to each non-observing region 52 at least in imaging under the imaging conditions. Specifically, acquisition limitation of output data of the non-observing elements is performed by stopping the operation of the non-observing elements or limiting the operation of each non-observing substrate. The above-described non-observing substrate means an A/D conversion substrate, which receives outputted signals from the non-observing elements, out of the respective A/D conversion substrates ADC1 to ADCn of the conversion-substrate set 71.

More specifically, the processing circuitry 76 limits the operation of each non-observing substrate by, e.g., shifting the operational state of each non-observing substrate to the operation-limited state (i.e., either the standby state or the stop state) so that each non-observing substrate stops at least the operation of outputting processed signals. Even if the operational state of each non-observing substrate is either the standby state or the stop state, power consumption of the X-ray CT apparatus 10 is reduced compared with a case where each non-observing substrate is in the normal operation state.

When the driving method of the A/D conversion substrates is the originally-OFF method, the processing circuitry 76 causes each A/D conversion substrate corresponding to the imaging region 51 to shift to the normal operation state and acquire output data of the X-ray detecting elements 33a, at least in imaging under the imaging conditions. In this control, since each non-observing substrate is in the operation-limited state, acquisition of output data of each non-observing element is logically limited.

In either driving method, the processing circuitry 76 limits acquisition of output data of each non-observing element and causes components for acquisition of output data of the X-ray detecting element 33a corresponding to the imaging region included in the imaging conditions to operate, in imaging under the imaging conditions. Consequently, power consumption of the X-ray CT apparatus 10 can be reduced compared with the case of causing all the X-ray detecting elements 33a to operate in imaging.

The memory circuitry 77 stores correspondence relationship between plural X-ray detecting elements 33a and the imaging region 51 to be set in imaging conditions of the object O (hereinafter, referred to as FOV-element relationship) in advance. Additionally, the memory circuitry 77 stores correspondence relationship between plural X-ray detecting elements 33a and plural A/D conversion substrates (hereinafter, referred to as element-substrate relationship) in advance. Those FOV-element relationship and element-substrate relationship are stored in, e.g., a table form in the memory circuitry 77.

Instead of those FOV-element relationship and element-substrate relationship or together with those FOV-element relationship and element-substrate relationship, the memory circuitry 77 stores correspondence relationship between the imaging region 51 and plural A/D conversion substrates (hereinafter, referred to as FOV-substrate relationship) in advance. The processing circuitry 76 can extract every non-observing substrate corresponding to each non-observing region 52 by using, e.g., information on these three types of correspondence relationship.

Incidentally, the information on these three types of correspondence relationship to be stored in the memory circuitry 77 may be stored in another memory circuit except the memory circuitry 77 (e.g., the memory circuit of the gantry control circuit 26 and/or the memory circuitry 43 of the console 13) and be arbitrarily provided to the DAS 34 via the gantry control circuit 26.

Figure 5:
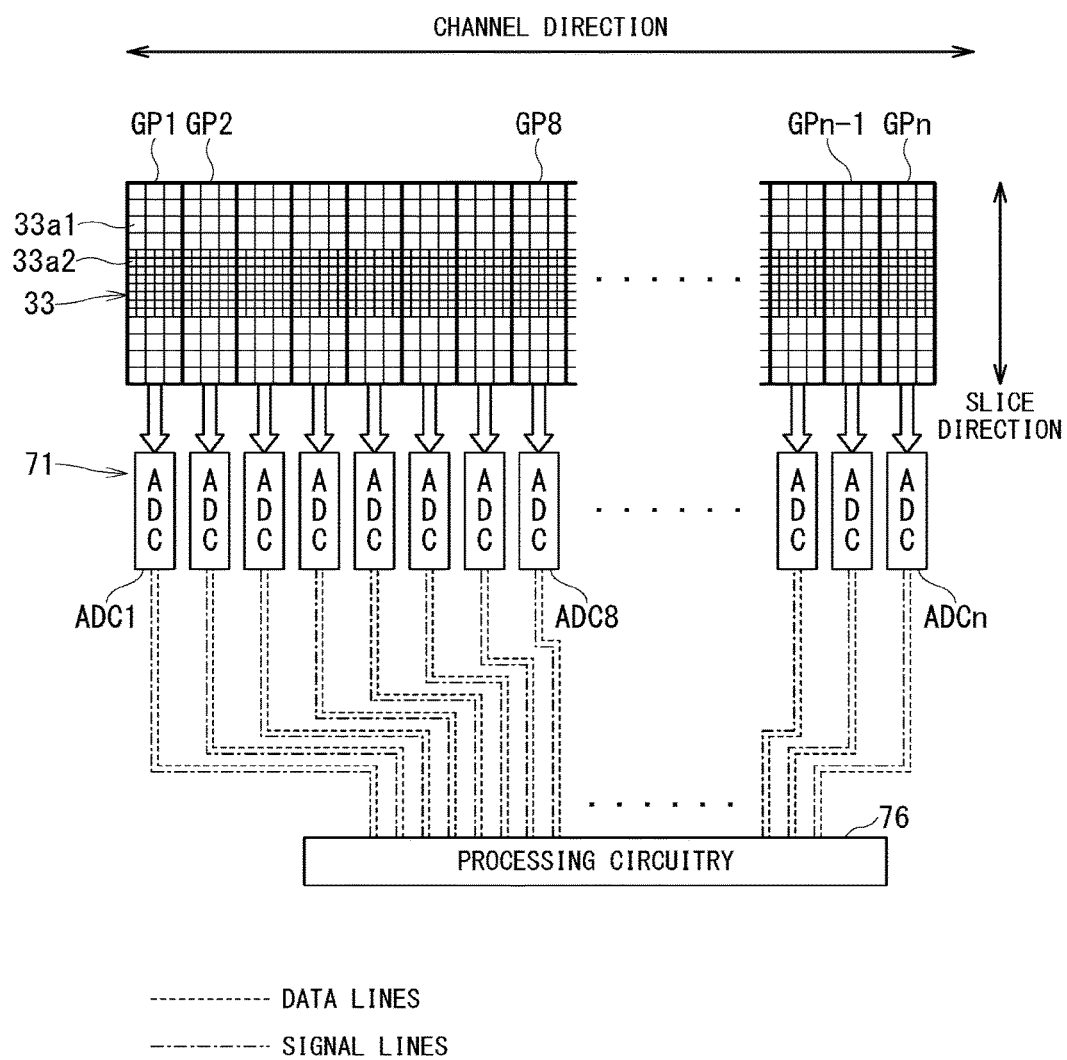
FIG. 5 is a schematic wiring diagram illustrating connection relationship of the X-ray detector, a conversion-substrate set, and processing circuitry.

FIG. 5 is a schematic wiring diagram illustrating connection relationship of the X-ray detector 33, the conversion-substrate set 71, and the processing circuitry 76. FIG. 5 shows a case where each X-ray detecting element 33a comprises elements 33a1 and elements 33a2, each of the elements 33a2 being smaller than each element 33a1 in size. FIG. 5 also shows a case where eight tiny elements 33a2 are arrayed at intervals of 0.5 mm in the central part in the slice direction and four elements 33a1 are arrayed at both end sides of those eight elements 33a2 at intervals of 1mm in the slice direction.

As shown in FIG. 5, the plural X-ray detecting elements 33a constituting the X-ray detector 33 are divided into n groups GP1, GP2, ..., GPn. The respective A/D conversion substrates ADC1 to ADCn of the conversion-substrate set 71 are connected to the X-ray detecting elements 33a so that the groups GP1 to GPn respectively correspond to the A/D conversion substrates ADC1 to ADCn. Note that the above-described groups are only conceptually dividing used for convenience in the present embodiment. Thus, it is not necessary that the plural X-ray detecting elements 33a are divided into plural groups each of which being physically separated from each other by, e.g., forming those X-ray detecting elements 33a on plural substrates corresponding to the respective groups.

Additionally, each of the A/D conversion substrates ADC1 to ADCn of the conversion-substrate set 71 is separately connected to the processing circuitry 76 via a data line indicated by a broken line and a signal line indicated by a chain line in FIG. 5. Each data line is a communication line for performing communication in which each A/D conversion substrate provides output data to the processing circuitry 76. Each signal line indicated by a chain line in FIG. 5 is used when the A/D conversion substrate is a non-observing substrate, in such a manner that the processing circuitry 76 transmits a command signal to limit the operation of this non-observing substrate.

Figure 6:
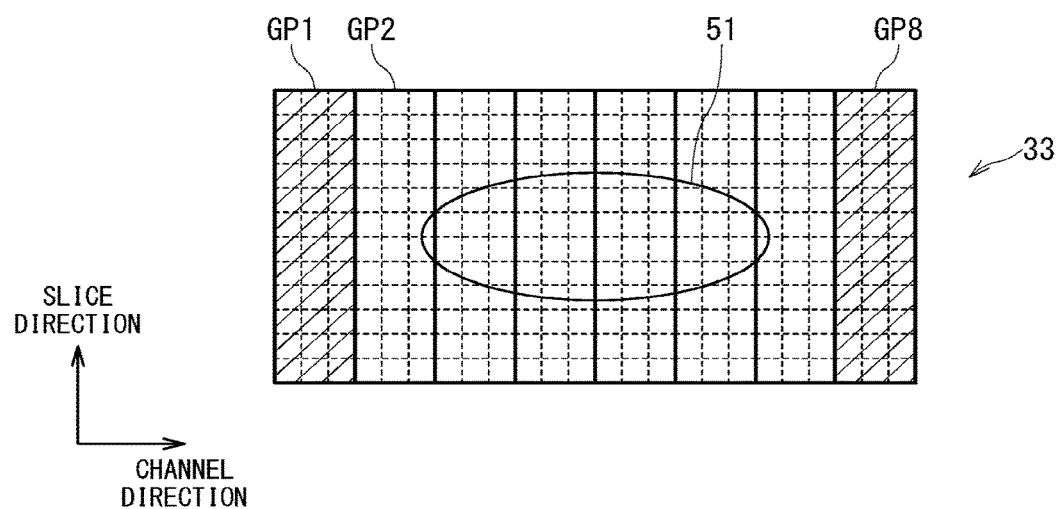
FIG. 6 is a schematic plan view illustrating relationship between an imaging region and each non-observing substrate.

FIG. 6 is a schematic plan view illustrating relationship between the imaging region 51 and the non-observing substrates. FIG. 6 shows a case where the plural X-ray detecting elements 33a indicated by broken-line squares can be divided into eight groups GP1 to GP8 indicated by bold-line rectangles along the channel direction. In this case, the conversion-substrate set 71 is configured of eight A/D conversion substrates ADC1 to ADC8 respectively corresponding to the eight groups GP1 to GP8.

In the case shown in FIG. 6, each of the groups GP1 and GP8 indicated by a hatched rectangular area is a group in which all the X-ray detecting elements 33a are non-observing elements. In this case, the processing circuitry 76 extracts the A/D conversion substrates ADC1 and ADC8 corresponding to those groups GP1 and GP8 as the non-observing substrates. In the case shown in FIG. 6, the non-observing substrates corresponding to the non-observing region 52 along the channel direction are extracted.

In FIG. 6, though a description has been given of a case where every A/D conversion substrate extracted as a non-observing substrate corresponds to a group in which all the X-ray detecting elements 33a are non-observing elements, each non-observing substrate may be extracted in the following manner. That is, every A/D conversion substrate corresponding to a group in which not all but some of the X-ray detecting elements 33a are non-observing elements may be additionally extracted as a non-observing substrate.

In the latter extraction method, the A/D conversion substrates ADC1, ADC2, ADC7, and ADC8 respectively corresponding to the groups GP1, GP2, GP7, and GP8 are extracted as the non-observing substrates in the case shown in FIG. 6.

In the former extraction method in which the A/D conversion substrates ADC1 and ADC8 are extracted as the non-observing substrates in the case of FIG. 6, all the imaging region 51 can be imaged and power consumption of the X-ray CT apparatus 10 can be reduced.

In the latter extraction method, though a peripheral part of the imaging region (FOV) is not sometimes imaged, power consumption of the X-ray CT apparatus 10 can be more reduced than the former extraction method. Since a region of interest (ROI) does not exist in an outer periphery part of an FOV in some cases, to use the latter extraction method in such cases does not cause a negative effect on reading.

Which one of the former and the latter extraction methods is used may be set by a user via the input circuit 41, for instance. Additionally, this setting may be included in imaging conditions of the imaging region.

A case is assumed when the A/D conversion substrate corresponding to a group including at least one non-observing element is extracted as a non-observing substrate. In this case, the A/D conversion substrate corresponding to a group in which the ratio of its non-observing element(s) to all the X-ray detecting elements 33a belonging to the group is equal to or more than a predetermined threshold value may only be extracted as a non-observing substrate.

Figure 7:
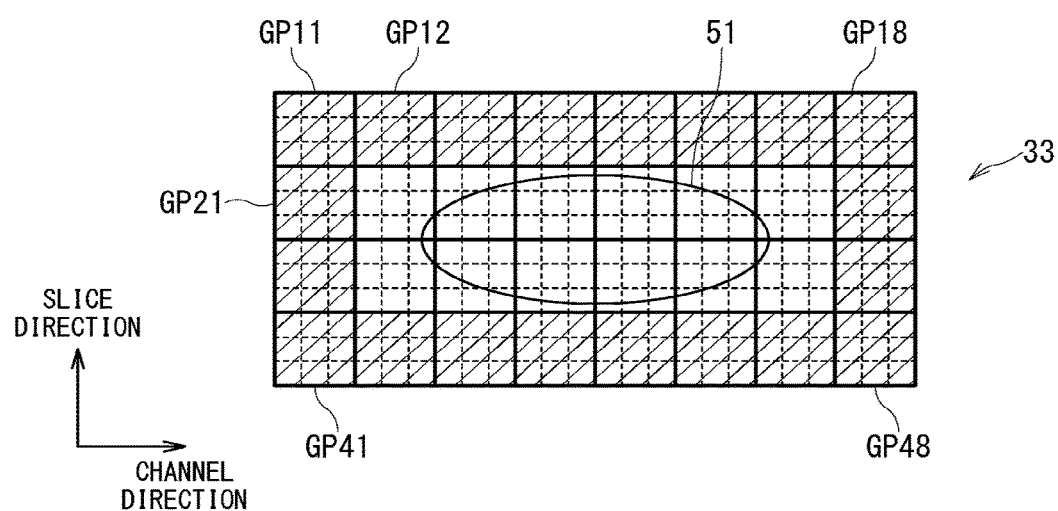
FIG. 7 is a schematic plan view illustrating another case of relationship between an imaging region and each non-observing substrate.

FIG. 7 is a schematic plan view illustrating another case of relationship between the imaging region 51 and the non-observing substrates. FIG. 7 shows a case where the plural X-ray detecting elements 33a are divided into 8 columns along the slice direction and 4 rows along the channel direction so as to be divided into a total of 32 groups. In FIG. 7, each of the X-ray detecting element 33a is indicated by a broken-line square and each of the 32 groups is indicated by a bold-line square. In this case, the conversion-substrate set 71 is configured of 32 A/D conversion substrates corresponding to the respective groups.

When the plural X-ray detecting elements 33a are divided along both of the channel direction and the slice direction, each non-observing substrate corresponding to the non-observing region 52 along the slice direction is extracted in addition to each non-observing substrate corresponding to the non-observing region 52 along the channel direction. In the case shown in FIG. 7, there are a total of 20 groups in each of which all the X-ray detecting element 33a belonging thereto are non-observing elements. Each of these 20 groups are indicated by a hatched square area in FIG. 7. In this case, the processing circuitry 76 extracts the respective A/D conversion substrates corresponding to these 20 groups as the non-observing substrates. In the case of FIG. 7, 62.5% of all the 32 groups, i.e., 20 groups are extracted. Thus, power consumption is more reduced than the case of FIG. 6 where 25% of all the 8 groups, i.e., 2 groups are extracted.

Also in the case of FIG. 7, every A/D conversion substrate corresponding to a group in which at least one the X-ray detecting element 33a belonging thereto is the non-observing element may be extracted as the non-observing substrate in a similar manner as described above.

Next, detailed configuration of the processing circuitry 76 will be described.

Figure 8:
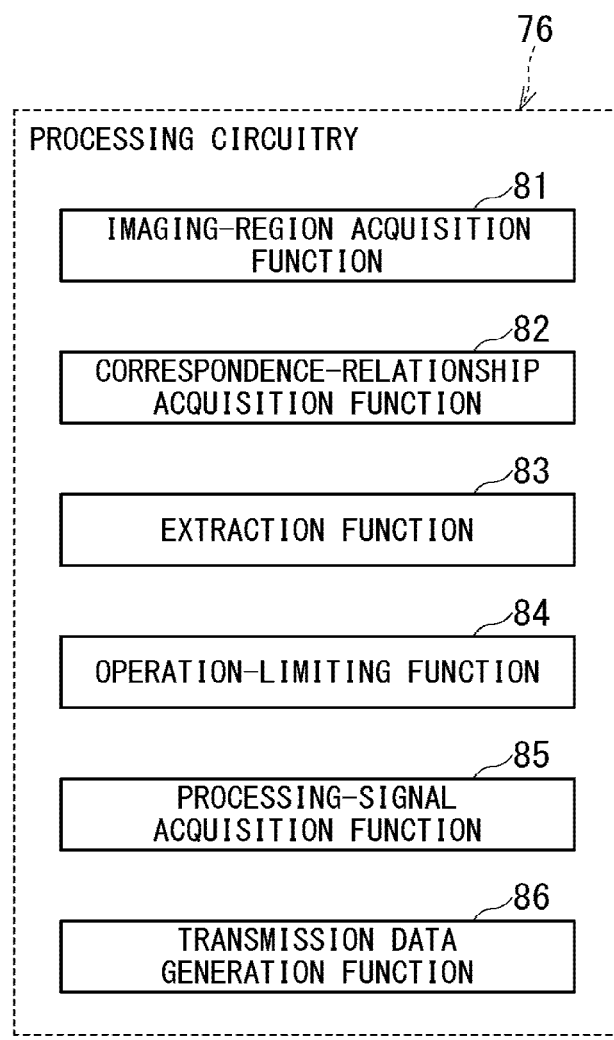
FIG. 8 is a block diagram illustrating functions implemented by the processing circuitry.

FIG. 8 is a block diagram illustrating functions implemented by the processing circuitry 76. The processing circuitry 76 implements at least an imaging-region acquisition function 81, a correspondence-relationship acquisition function 82, an extraction function 83, an operation-limiting function 84, a processing-signal acquisition function 85, and a transmission data generation function 86. These functions 81 to 86 are stored in the memory circuitry 77 in the form of programs.

The processing circuitry 76 performs processing of reducing power consumption of the X-ray CT apparatus 10 based on these functions 81 to 86 in at least imaging under imaging conditions, by causing to operate only the components relevant to acquisition of output data of the X-ray detecting elements 33a corresponding to the imaging region 51 included in the imaging conditions. Specifically, the processing circuitry 76 can achieve the above-described processing by limiting the operation of a non-observing element or a non-observing substrate at least in imaging under imaging conditions.

For instance, when the driving method of the A/D conversion substrates is the originally-ON method, the processing circuitry 76 limits the acquisition operation of output data of the X-ray detecting elements 33a corresponding to non-observing region 52 at least in imaging under imaging conditions. Acquisition limitation of output data of the non-observing elements can be performed by, e.g., limiting the operation of every A/D conversion substrate disposed at the post-stage of the non-observing elements.

Additionally, when the X-ray detecting elements 33a are driven by TFT (Thin-Film-Transistor) thereby consuming electric power in operation, the processing circuitry 76 may control the X-ray detector 33 by stopping power-supply to each non-observing element so as to stop the operation of each non-observing element. Acquisition Limitation of output data of each non-observing element is performed by, e.g., at least one of processing of limiting the operation of the A/D conversion substrate(s) and processing of stopping the operation of each non-observing element. In the present embodiment, a description will be given of a case where acquisition limitation of output data of the non-observing elements is performed by limiting the operation of the A/D conversion substrate(s) disposed at the post-stage of the non-observing elements.

The imaging-region acquisition function 81 is a function of acquiring information on the imaging region 51 included in imaging conditions from the console 13 via the gantry control circuit 26 and inputting this acquired information to the extraction function 83. In imaging conditions, positional information on the imaging region 51 (FOV) in terms of the channel direction and the slice direction is included.

Even the situation where the imaging conditions are being set and the imaging region 51 has not yet been set but an anatomical imaging part have already been set, the imaging-region acquisition function 81 may estimate the imaging region 51 based on the set anatomical imaging part of the object and provide the information on the estimated imaging region 51 to the extraction function 83. For instance, when the size of the imaging region 51 is selected from one of "Large", "Medium", and "Small", the imaging-region acquisition function 81 may estimate the size of the imaging region 51 to be "Medium" in the case where the head is set as the anatomical imaging part, and may estimate the size of the imaging region 51 to be "Large" in the case where the trunk of the body is set as the anatomical imaging part. In this manner, the imaging-region acquisition function 81 can estimate the imaging region 51 according to the anatomical imaging part. Also in this case, it is desirable that the memory circuitry 77 preliminarily or previously stores correspondence relationship between each anatomical imaging part and possible imaging regions 51.

Consider a case where the imaging region 51 is estimated on the basis of the information on the anatomical imaging part in such a period that setting of imaging conditions are performed and the imaging region 51 is neither set nor determined. In this case, if the driving method of the A/D conversion substrates is the originally-ON method, power consumption can be more reduced by starting limitation of the operation of every non-observing substrate before setting of all the imaging conditions are completed. Also in this case, if the driving method of the A/D conversion substrates is the originally-OFF method, imaging can be started immediately after determination of all the imaging conditions because the A/D conversion substrates corresponding to the imaging region 51 can be shifted to the normal operation state and be warmed up before completion of setting all the imaging conditions.

The correspondence-relationship acquisition function 82 is a function of acquiring the FOV-element relationship and the element-substrate relationship from the memory circuitry 77. Additionally, when the FOV-substrate relationship is stored in the memory circuitry 77, the correspondence-relationship acquisition function 82 has a function of acquiring the FOV-substrate relationship from the memory circuitry 77.

The extraction function 83 is a function of extracting the non-observing elements corresponding to the non-observing region 52 or extracting each non-observing substrate corresponding to those non-observing elements, on the basis of information on the imaging region 51 inputted from the console 13 via the imaging-region acquisition function 81. In this extraction, the extraction function 83 may preferably use the FOV-substrate relationship received from the correspondence-relationship acquisition function 82, for instance. Additionally, when the extraction function 83 receives the FOV-element relationship and the element-substrate relationship from the correspondence-relationship acquisition function 82, the extraction function 83 may determine the FOV-substrate relationship based on the received information.

The operation-limiting function 84 controls the operation of each non-observing element or each non-observing substrate in at least imaging under imaging conditions. The operation-limiting function 84 controls the operation of each non-observing substrate in at least imaging under imaging conditions so that each non-observing substrate stops at least output of processed signals. Limitation of the operation of each non-observing substrate is performed by limiting the operational state of each non-observing substrate so that each non-observing substrate stops at least output of processed signals. Additionally, the operation-limiting function 84 may control each non-observing element in at least imaging under imaging conditions so as to, e.g., stop the operation of each non-observing element.

More specifically, when the driving method of the A/D conversion substrates is the originally-ON method, the processing circuitry 76 communicates with each non-observing substrate via the signal line by the operation-limiting function 84 in at least imaging under imaging conditions. Afterward, the processing circuitry 76 limits the operation of each non-observing substrate so as to stop at least output of processed signals by shifting the operational state of each non-observing substrate to the standby state or the stop state. The shift of the operational state of each non-observing substrate to the stop state is performed by stopping power-supply to each non-observing substrate. When the number of the non-observing substrates is two or more, the processing circuitry 76 may shift one or some of those two or more non-observing substrates to the standby state and shift the rest of those non-observing substrates to the stop state.

Additionally, when the driving method of the A/D conversion substrates is the originally-OFF method, the processing circuitry 76 communicates with each A/D conversion substrate corresponding to the imaging region 51 via the signal line by the operation-limiting function 84 in at least imaging under imaging conditions, causes each A/D conversion substrate corresponding to the imaging region 51 to shift to the normal operation state. Thereby, the processing circuitry 76 causes each A/D conversion substrate corresponding to the imaging region 51 to acquire output data of the X-ray detecting elements 33a.

The processing signal acquisition function 85 is a function of communicating with the conversion-substrate set 71 via the data lines, receiving processed signals from the A/D conversion substrates except the non-observing substrate(s), and inputting the received signals to the transmission data generation function 86.

Additionally, as to communication with each A/D conversion substrate extracted as the non-observing substrate via the data line, the processing signal acquisition function 85 has a function of performing error-masking processing. Any signal cannot be received via the data line from each A/D conversion substrate extracted as the non-observing substrate. This is because each non-observing substrate is caused to stop at least the operation of outputting processed signals by the operation-limiting function 84. If there is a data line from which any signal is not transmitted, there is a possibility that the processing circuitry 76 incorrectly recognizes occurrence of communication error such as interruption of communication. Hence, it is desirable that the processing signal acquisition function 85 applies error-masking processing to each data line, out of all the data lines, via which each non-observing substrate and the processing circuitry 76 communicates, whereby the processing circuitry 76 can prevent erroneous recognition of the occurrence of communication interruption.

The transmission data generation function 86 is a function of generating the transmission data by using processed signals outputted from the conversion-substrate set 71 and transmitting the generated transmission data to the console 13 via the data transmission device 27.

The console 13 may command that the gantry control circuit 26 and the DAS 34 should use only projection data of the A/D conversion substrates corresponding to the imaging region 51 and add dummy data to data of the rest of the A/D conversion substrates, for instance. In this case, the transmission data generation function 86 adds dummy data to such a position in data-structure of the transmission data that a processed signal corresponding to each non-observing substrate whose operation is limited by the operation-limiting function 84 should be arranged. As the dummy data, for instance, a test pattern (such as random data) used for confirming establishment of communication connection between the processing circuitry 76 of the DAS control substrate 72 and the console 13 may be used. The console 13 can perform reconstruction processing based on the projection data included in the transmission data so as to generate reconstructed images.

Next, an operation performed by the X-ray CT apparatus 10 of the present embodiment will be described.

Figure 9:
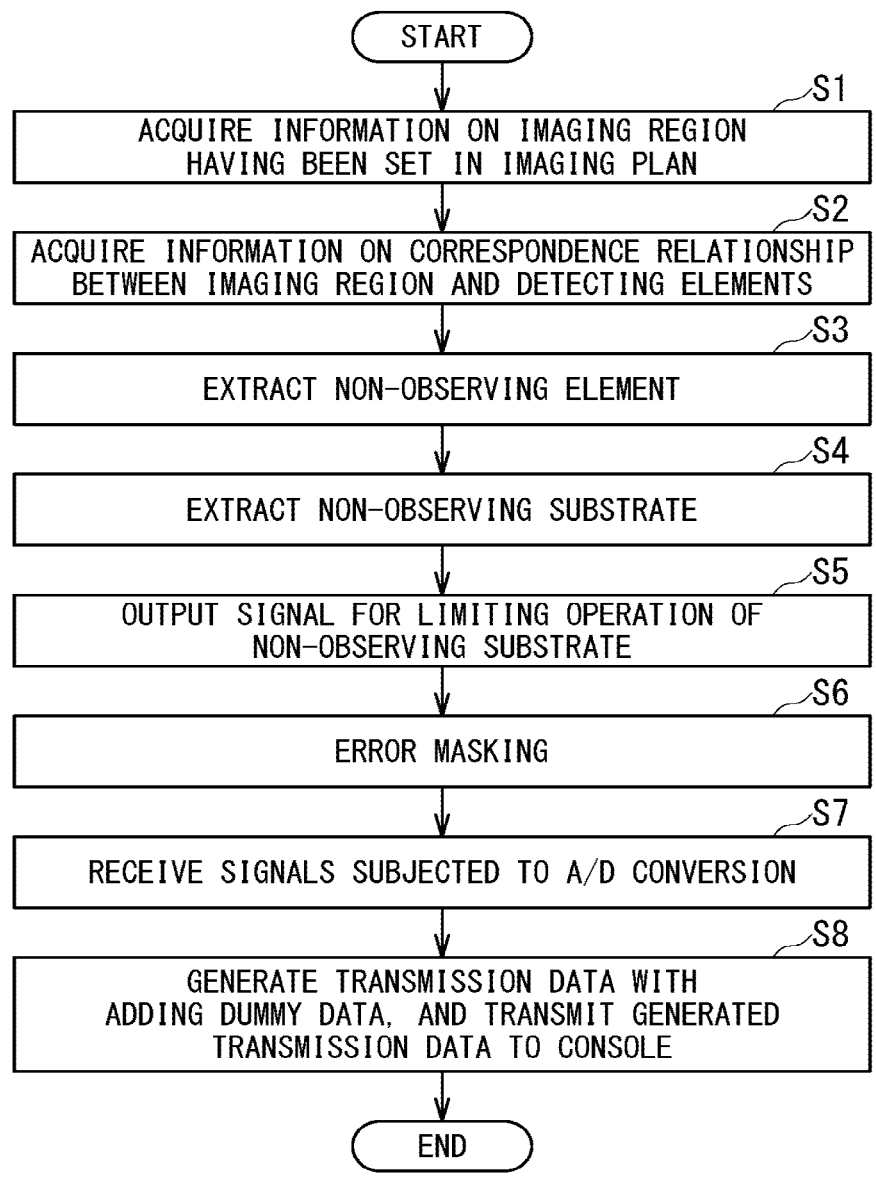
FIG. 9 is a flowchart illustrating processing of reducing power consumption of the X-ray CT apparatus in such a manner that the processing circuitry of the DAS limits an operation of each non-observing substrate by causing each non-observing substrate to stop at least an operation of outputting processed signals.

FIG. 9 is a flowchart illustrating processing of reducing power consumption of the X-ray CT apparatus 10 in such a manner that the processing circuitry 76 of the DAS 34 limits the operation of each non-observing substrate by causing each non-observing substrate to stop at least the operation of outputting processed signals. In FIG. 9, each reference symbol consisting of S and number on its right side indicates each step of the flowchart. FIG. 9 shows a case where the driving method of the A/D conversion substrates is the originally-ON method and each non-observing substrate is caused to stop at least output of processed signals by being limited under the originally-ON method.

The processing shown in FIG. 9 starts when the console 13 receives setting of imaging conditions including positional information of the imaging region (FOV) in terms of the channel direction and the slice direction determined by a user via the input circuit 41.

First, in the step S1, the processing circuitry 76 acquires information on the imaging region 51 included in imaging conditions from the console 13 via the gantry control circuit 26, by its imaging-region acquisition function 81.

Next, in the step S2, the processing circuitry 76 acquires the FOV-element relationship and the element-substrate relationship from the memory circuitry 77 by its correspondence-relationship acquisition function 82.

Next, in the step S3, the processing circuitry 76 extracts every non-observing element by its extraction function 83, on the basis of the FOV-element relationship and the information on the imaging region 51.

Next, in the step S4, the processing circuitry 76 extracts every non-observing substrate by the extraction function 83, on the basis of the element-substrate relationship and the non-observing elements extracted in the step S3. Incidentally, when the FOV-substrate relationship is available, the processing circuitry 76 may directly extract every non-observing substrate by its extraction function 83 on the basis of information on the imaging region 51 and the FOV-substrate relationship, instead of executing the processing of the steps S3 and S4.

Next, in the step S5, the processing circuitry 76 communicates with each non-observing substrate via the signal line and shifts the operational state of each non-observing substrate to the standby state or the stop state so as to cause each non-observing substrate to stop at least output of processed signals. This processing in the step S5 corresponds to the operation-limiting function 84 of the processing circuitry 76.

Next, in the step S6, the processing circuitry 76 applies error-masking processing to communication via the respective data lines connected with the non-observing substrates, by its processing signal acquisition function 85.

Next, in the step S7, the processing circuitry 76 communicates with the conversion-substrate set 71 via the data lines and receives processed signals from the A/D conversion substrates excluding the non-observing substrates, by its processing signal acquisition function 85.

Next, in the step S8, the processing circuitry 76 generates the transmission data by using the processed signals outputted from the conversion-substrate set 71 and transmits the generated transmission data to the console 13 via the data transmission device 27, by its the transmission data generation function 86. In this case, the processing circuitry 76 adds dummy data to such a position in data-structure of the transmission data that a processed signal corresponding to each non-observing substrate whose operation is limited by the operation-limiting function 84 should be arranged.

According to the above-described method, power consumption of the X-ray CT apparatus 10 can be reduced by limiting the operation of each non-observing substrate in such a manner that each non-observing substrate is caused to stop at least output of processed signals.

Figure 10:
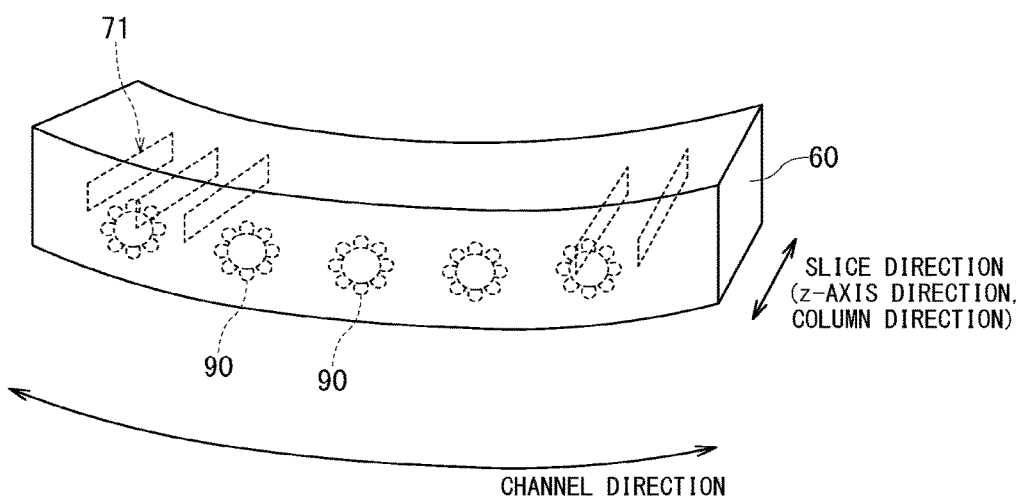
FIG. 10 is a schematic perspective view illustrating a housing in which the X-ray detector and the DAS are housed further houses plural fans.

FIG. 10 is a schematic perspective view illustrating the housing 60 in which the X-ray detector 33 and the DAS 34 are housed further houses plural fans 90.

As shown in FIG. 10, plural fans 90 configured to emit heat generated by the respective A/D conversion substrates may be provided near the conversion-substrate set 71. Each of the fans 90 can emit the heat generated by the A/D conversion substrates positioned adjacent thereto from a non-illustrated outlet of the housing 60.

When the X-ray CT apparatus 10 is equipped with these plural fans 90, the processing circuitry 76 can further reduce power consumption of the X-ray CT apparatus 10 by stopping the operation of the fan(s) 90 corresponding to all the non-observing substrates in the step S5 of FIG. 9.

Additionally, the conversion-substrate set 71 may be divided into plural groups so that the fans 90 correspond to the respective substrate groups. In this case, one fan 90 cools down plural A/D conversion substrates which belong to the substrate group corresponding to this fan 90. It is preferable that the operation-limiting function 84 reduces power consumption of the X-ray CT apparatus 10 by stopping the operation of every fan 90 corresponding to a substrate group in which all the A/D conversion substrates belonging thereto are non-observing substrates. The operation-limiting function 84 causes every fan 90 corresponding to a group in which all the A/D conversion substrates correspond to the imaging region 51 to normally operate.

As to a group in which at least one A/D conversion substrate corresponds to the imaging region 51 is included, the operation-limiting function 84 may preferably cause each fan 90 corresponding to such a group to activate. Further, as to a group in which non-observing substrate and A/D conversion substrate corresponding to the imaging region 51 are both included, the operation-limiting function 84 may intermittently activate each fan 90 corresponding to such a group. This intermittent operation may be performed in a predetermined cycle or may be performed according to a substrate temperature. The predetermined cycle is preferably set so that the operation time of each fan becomes longer as more substrate corresponds to the imaging region 51.

Figure 11:
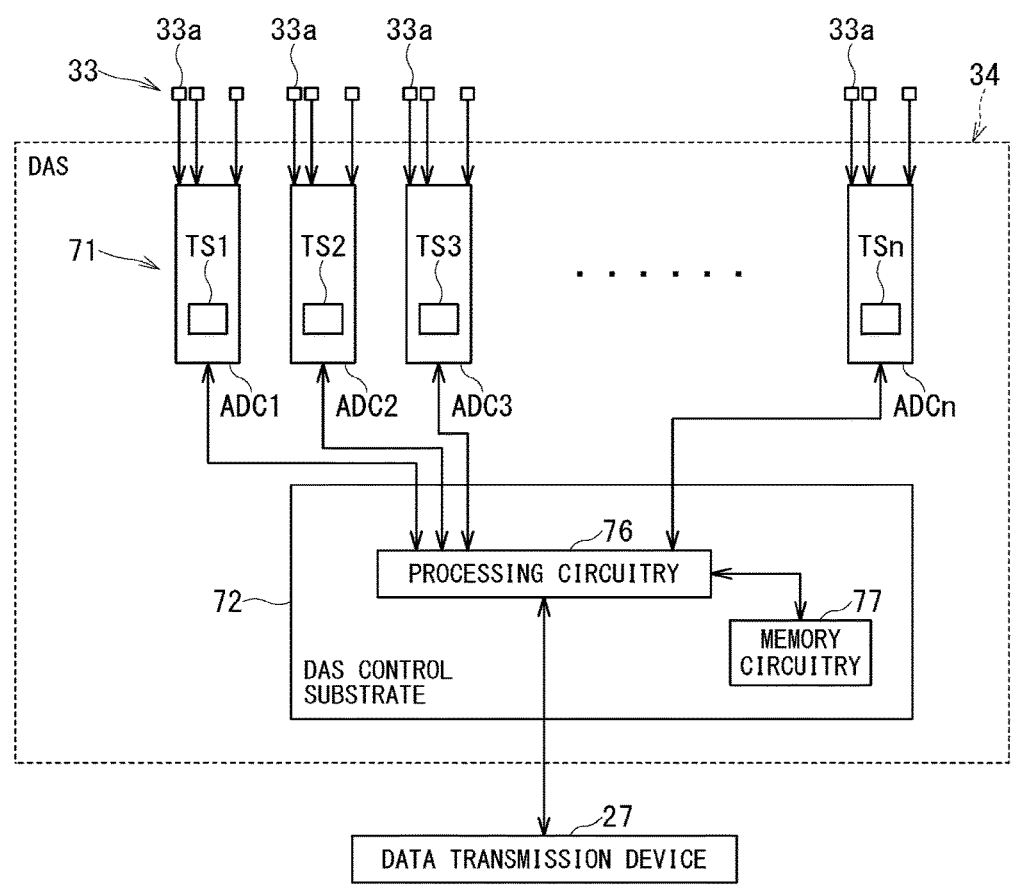
FIG. 11 is a block diagram illustrating a modification of internal configuration of the DAS.

FIG. 11 is a block diagram illustrating a modification of internal configuration of the DAS 34.

The X-ray CT apparatus 10 may further include n temperature sensors TS1 to TSn. The temperature sensors TS1 to TSn respectively measures temperatures of the A/D conversion substrates ADC1 to ADCn of the conversion-substrate set 71, and input the measured temperatures to the operation-limiting function 84.

When the X-ray CT apparatus 10 includes the temperature sensors TS1 to TSn, the operation-limiting function 84 may preferably control the operation of each fan 90 according to the temperature of each of the A/D conversion substrates.

For instance, as to a group in which non-observing substrate and A/D conversion substrate corresponding to the imaging region 51 are both included, the operation-limiting function 84 acts according to the following points. Firstly, the operation-limiting function 84 monitors the temperature of each A/D conversion substrate corresponding to the imaging region 51 in such a group. Secondly, when the temperature of at least one A/D conversion substrate corresponding to the imaging region 51 in such a group is equal to or higher than the first predetermined temperature, the operation-limiting function 84 activates the fan 90 corresponding to such a group, while the operation-limiting function 84 stops the operation of the fan 90 corresponding to such a group in a period during which the temperatures of all the A/D conversion substrates corresponding to the imaging region 51 in such a group are lower than the first predetermined temperature, thereby intermittently activate each fan 90 corresponding to such a group. In this case, the operation-limiting function 84 may exclude the temperatures of the non-observing substrates belonging to such a group from monitoring targets.

Additionally, when the X-ray CT apparatus 10 includes the temperature sensors TS1 to TSn, the operation-limiting function 84 may preferably control the operational state of each A/D conversion substrate according to the temperature thereof so that the temperature of each A/D conversion substrate does not drop excessively. It is preferable that the temperature of each of the X-ray detecting elements 33a is in a temperature range appropriate for detecting X-rays. However, when a certain A/D conversion substrate is in the operation-limited state (i.e., the stop state or the standby state) and its substrate temperature drops, the respective temperatures of the X-ray detecting elements 33a connected to this A/D conversion substrate drop in some cases.

For instance, when a non-observing region changes to the imaging region 51 in short time such as a case where plural protocols with imaging regions 51 positionally different from each other are set in one sequence, a non-observing element changes to an observing element in short time. If the temperature of this observing element shortly after being changed from a non-observing element is lowered, imaging cannot be resumed in some cases until the temperature of this observing element increased to a temperature range appropriate for detecting X-rays due to thermal conduction. In other words, unless the A/D conversion substrate including this observing element shifts to the normal operation state so as to heat up and cause the temperature of this observing element to increase to the above-described appropriate temperature range due to thermal conduction, imaging cannot be resumed.

Further, the X-ray CT apparatus 10 may be equipped with a heater for keeping the temperatures of the respective X-ray detecting elements 33a within a temperature range appropriate for detecting X-rays. When temperature control of all the components of the X-ray detector 33 is performed by only one heater in this case, temperature non-uniformity is caused between the X-ray detecting elements 33a constituting the X-ray detector 33. For instance, when the temperature of the X-ray detector 33 partially drops due to temperature decrease of non-observing elements, the one heater operates to keep the temperature of this decreased-temperature area including those non-observing elements within the above-described appropriate range. Consequently, the respective temperatures of the X-ray detecting elements 33a corresponding to the imaging region 51 excessively increase.

For this reason, it is preferable that the operation-limiting function 84 intermittently increases power-supply to each A/D conversion substrate in the operation-limited state in the conversion-substrate set 71. Specifically, as to each A/D conversion substrate which is in the operation-limited state and has temperature lower than the second predetermined temperature, it is preferable to cause such an A/D conversion substrate to shift to the normal operation state. When the temperature of such an A/D conversion substrate shifted to the normal operation state in the above manner increases and becomes higher than the third predetermined temperature which is higher than the second predetermined temperature, it is preferable to cause such an A/D conversion substrate to shift to the operation-limited state again. By performing the above-described control of intermittent power-supply, the respective temperatures of the A/D conversion substrates can be kept within a predetermined temperature range so that the respective temperatures of the X-ray detecting elements 33a are kept within a temperature range appropriate for detecting X-rays.

According to at least one of the above-described embodiments, only the components relevant to acquisition of output data of detecting elements corresponding to the imaging region included in imaging conditions can be caused to operate in imaging based on the imaging conditions.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For instance, it is enough that the radiation diagnostic apparatus of the present embodiment includes plural radiation detecting elements, plural data processing circuits (i.e., signal processing substrate) as control targets of the present embodiment such as A/D converters and current/voltage converters receiving data from those detecting elements, and a control system configured to appropriately process output data from these data processing circuits.

Although a description has been given of a case where the X-ray CT apparatus 10 equipped with the X-ray detector 33 for an X-ray CT imaging is used for a radiation diagnostic apparatus and this X-ray detector 33 includes plural X-ray detecting elements 33a arranged in two-dimensional array along the slice direction and the channel direction in the present embodiment, radiation diagnostic apparatuses of the present embodiment are not limited to an X-ray CT apparatus.

For instance, any X-ray angiographic apparatus or X-ray diagnostic apparatus which includes an FPD (Flat Panel Detector) configured of plural detecting elements, plural data processing circuits disposed at the post-stage of the FPD, and a control system configured to appropriately process output data from these data processing circuits can be used as a radiation diagnostic apparatus of the present embodiment.

The processing circuitry 76 in the above-described embodiment is an example of the processing circuitry recited in the claims. Additionally, the term "processor" used for the description of the gantry control circuit 26, the general control circuit 44, and the processing circuitry 76 in the present embodiment means, e.g., a circuit such as a special-purpose or general-purpose CPU (Central Processing Unit), a special-purpose or general-purpose GPU (Graphics Processing Unit), an ASIC (Application Specific Integrated Circuit), a programmable logic device including an SPLD (Simple Programmable Logic Device) and a CPLD (Complex Programmable Logic Device), and an FPGA (Field Programmable Gate Array). A processor implements various types of functions by reading out programs stored in a memory circuit and executing the programs.

Additionally, programs may be directly installed in the circuit of the processor instead of storing programs in the memory circuit. In this case, the processor implements various types of functions by reading out programs stored in its own circuit and executing the programs.

In FIG. 4, though a description has been given of a case where all the required functions are implemented by only the processing circuitry 76, the processing circuitry 76 may be configured by combining plural processors independent of each other so that each function of the processing circuitry 76 is implemented by causing each of the processors to execute the program corresponding each function.

Further, when plural processors are provided for the processing circuitry, a memory medium for storing the programs may be provided for each processor or the memory circuitry 77 in FIG. 4 may collectively store all the programs corresponding to all the functions of the processors.

What is claimed is:

1. A radiation diagnostic apparatus comprising:
an X-ray tube;
a plurality of radiation detecting elements configured to detect X-rays radiated from the X-ray tube;
a plurality of signal processing substrates configured to perform processing including at least A/D conversion processing on outputted signals of the plurality of radiation detecting elements and to output processed signals as the outputted signals after being subjected to the processing including at least A/D conversion; and
processing circuitry configured to
identify a non-observing element or a non-observing substrate based on information on an imaging region included in imaging conditions of an object, the non-observing element being a radiation detecting element of the plurality of radiation detecting elements which corresponds to a region other than the imaging region, and the non-observing substrate being a signal processing substrate of the plurality of signal processing substrates which corresponds to the non-observing element, and
control an operation of the non-observing element or an operation of the non-observing substrate in imaging under the imaging conditions.

2. The radiation diagnostic apparatus according to claim 1,
wherein the processing circuitry is configured to
control a radiation detecting element and a signal processing substrate each corresponding to the imaging region in imaging under the imaging conditions such that the radiation detecting element and the signal processing substrate each corresponding to the imaging region are both in a normal operation state in which the processed signals are outputted, and
control the non-observing element or the non-observing substrate in imaging under the imaging conditions, so as to limit an operation of acquiring output data of the non-observing element, such that the non-observing element is in a stop state in which the non-observing element stops its operations or the non-observing substrate is in an operation-limited state in which the non-observing substrate at least stops outputting the processed signals.

3. The radiation diagnostic apparatus according to claim 2, wherein the processing circuitry is configured to, when all of the plurality of signal processing substrates are in the normal operation state before setting of the imaging conditions, control the non-observing element or the non-observing substrate in imaging under the imaging conditions, so as to limit the operation of acquiring output data of the non-observing element, such that the non-observing substrate shifts to the operation-limited state or the non-observing element shifts to the stop state.

4. The radiation diagnostic apparatus according to claim 2, wherein the processing circuitry is configured, when all of the plurality of signal processing substrates are in the operation-limited state before setting of the imaging conditions, to make the signal processing substrate corresponding to the imaging region shift to the normal operation state in imaging under the imaging conditions, and to control the non-observing element or the non-observing substrate in imaging under the imaging conditions, so as to limit the operation of acquiring output data of the non-observing element, such that the non-observing substrate shifts to the operation-limited state or the non-observing element shifts to the stop state.

5. The radiation diagnostic apparatus according to claim 2, wherein the operation-limited state of the non-observing substrate is a stop state in which the non-observing substrate stops its operations and power-supply to the non-observing substrate is stopped.

6. The radiation diagnostic apparatus according to claim 2, wherein the operation-limited state of the non-observing substrate is a standby state in which the non-observing substrate stops at least an operation of outputting the processed signals.

7. The radiation diagnostic apparatus according to claim 2, wherein the processing circuitry is configured to generate transmission data based on the processed signals outputted from the plurality of signal processing substrates, by communicating with the plurality of signal processing substrates with applying error-masking processing to communication with the non-observing substrate of the operation-limited state.

8. The radiation diagnostic apparatus according to claim 2, further comprising a console configured to output setting information of the imaging conditions to the processing circuitry,
wherein the processing circuitry is configured to
generate transmission data based on the processed signals outputted from the plurality of signal processing substrates such that dummy data is added only to the transmission data corresponding to the non-observing substrate of the operation-limited state, and
transmit the generated transmission data to the console.

9. The radiation diagnostic apparatus according to claim 1, wherein:
the plurality of radiation detecting elements are divided into a plurality of element groups;
each of the plurality of signal processing substrates is connected with radiation detecting elements such that the each of the plurality of signal processing substrate is corresponding to each element group of the plurality of element groups; and
the processing circuitry is configured to identify a signal processing substrate as the non-observing substrate when all radiation detecting elements of an element group that corresponds to said signal processing substrate are positioned outside the imaging region.

10. The radiation diagnostic apparatus according to claim 1, wherein:
the plurality of radiation detecting elements are arranged in two-dimensionally in a first axis direction and a second axis direction; and
the processing circuitry is configured to identify the non-observing substrate corresponding to a region which is positioned outside the imaging region along at least one of the first axis direction and the second axis direction.

11. The radiation diagnostic apparatus according to claim 10, wherein:
the plurality of radiation detecting elements comprises an X-ray detector of an X-ray CT apparatus;
the first axis is one of a channel direction axis and a slice direction axis, while the second axis is another of the channel direction axis and the slice direction axis; and
the processing circuitry is configured to identify the non-observing substrate corresponding to a region which is positioned outside the imaging region in at least a direction along the channel direction axis.

12. The radiation diagnostic apparatus according to claim 1, further comprising memory circuitry configured to store in advance a correspondence relationship between the plurality of signal processing substrates and the imaging region being set in the imaging conditions.

13. The radiation diagnostic apparatus according to claim 1, further comprising a plurality of fans configured to discharge heat generated by the plurality of signal processing substrates,
wherein the processing circuitry is configured to stop a fan corresponding to the non-observing substrate out of the plurality of fans.

14. The radiation diagnostic apparatus according to claim 13, wherein:
the plurality of signal processing substrates are divided into a plurality of substrate groups;
each of the plurality of fans is corresponding to each substrate group of the plurality of substrate groups; and
the processing circuitry is configured to stop a fan when all signal processing substrate of a substrate group that corresponds to said fan are the non-observing substrates.

15. The radiation diagnostic apparatus according to claim 14, further comprising a temperature sensor configured to measure a temperature of each of the plurality of signal processing substrates and to output a measurement result to the processing circuitry,
 wherein the processing circuitry is configured to activate a fan corresponding to a substrate group that includes both the non-observing substrate and a signal processing substrate corresponding to the imaging region when a temperature of the signal processing substrate corresponding to the imaging region of said substrate group is equal to or higher than the predetermined temperature, and is configured to stop said fan when said temperature is lower than the predetermined temperature.

16. The radiation diagnostic apparatus according to claim 2, further comprising a temperature sensor configured to measure a temperature of each of the plurality of signal processing substrates and to output a measurement result to the processing circuitry,
 wherein the processing circuitry is configured to make a signal processing substrate in the operation-limited state shift to a normal operation state when a temperature of said signal processing substrate in the operation-limited state is lower than a predetermined temperature.

17. The radiation diagnostic apparatus according to claim 1,
 wherein the processing circuitry is configured to estimate, when an imaging part of the object in the imaging conditions is set, the imaging region from the set imaging part of the object, and to identify the non-observing element or the non-observing substrate based on the estimated imaging region.

* * * * *